(12) United States Patent
Pauws et al.

(10) Patent No.: US 10,395,202 B2
(45) Date of Patent: Aug. 27, 2019

(54) METHOD AND SYSTEM FOR DETERMINING PATIENT STATUS

(71) Applicant: KONINKLIJKE PHILIPS N.V., Eindhoven (NL)

(72) Inventors: Steffen Clarence Pauws, Eindhoven (NL); Alphonsus Anghonius Jozef De Lange, Overpelt (BE); Cornelis Conradus Adrianus Maria Van Zon, Fishkill, NY (US); Pradyumna Dutta, Bedford Corners, NY (US); William Palmer Lord, Fishkill, NY (US)

(73) Assignee: Koninklijke Philips N.V., Eindhoven (NL)

( * ) Notice: Subject to any disclaimer, the term of this patent is extended or adjusted under 35 U.S.C. 154(b) by 644 days.

(21) Appl. No.: 14/427,792

(22) PCT Filed: Sep. 27, 2013

(86) PCT No.: PCT/IB2013/058933
§ 371 (c)(1),
(2) Date: Mar. 12, 2015

(87) PCT Pub. No.: WO2014/049564
PCT Pub. Date: Apr. 3, 2014

(65) Prior Publication Data
US 2015/0317578 A1   Nov. 5, 2015

Related U.S. Application Data

(60) Provisional application No. 61/707,168, filed on Sep. 28, 2012.

(51) Int. Cl.
*G06F 19/00* (2018.01)
*G06Q 10/06* (2012.01)
(Continued)

(52) U.S. Cl.
CPC ....... *G06Q 10/0637* (2013.01); *G06F 19/325* (2013.01); *G06Q 10/10* (2013.01); *G06Q 50/22* (2013.01); *G16H 50/20* (2018.01)

(58) Field of Classification Search
CPC ............. G06Q 50/22–24; G06Q 10/10; G06Q 10/0637; G16H 50/20; G06F 19/325
(Continued)

(56) References Cited

U.S. PATENT DOCUMENTS 6,311,180 B1 * 10/2001 Fogarty ............... G06F 16/9577
707/749
2002/0019749 A1   2/2002 Becker et al.
(Continued)

FOREIGN PATENT DOCUMENTS

CN       1330342 A    1/2002
CN     101086785 A   12/2007
(Continued)

*Primary Examiner* — Joy Chng

(57) ABSTRACT

A system, method and tangible computer readable storage medium for storing a computer-implemented guideline, wherein the computer-implemented guideline includes a plurality of device independent nodes, determining a current state of the computer-implemented guideline, wherein the current state relates to one of the device independent nodes, retrieving device features relating to a device on which the one of the device independent nodes of the computer-implemented guideline is to be performed, modifying the one of the device independent nodes based on the device features to generate a device specific node and instantiating the device specific node on the device.

16 Claims, 5 Drawing Sheets

(51) Int. Cl.
    *G06Q 10/10*     (2012.01)
    *G06Q 50/22*     (2018.01)
    *G16H 50/20*     (2018.01)

(58) Field of Classification Search
    USPC ........................................................ 705/2–3
    See application file for complete search history.

(56) References Cited

U.S. PATENT DOCUMENTS

| | | | |
|---|---|---|---|
| 2005/0119914 A1 | 6/2005 | Batch | |
| 2005/0131741 A1 | 6/2005 | Paul et al. | |
| 2005/0171815 A1 | 8/2005 | Vanderveen | |
| 2006/0173713 A1* | 8/2006 | Petro | G16H 40/20 705/2 |
| 2009/0036750 A1* | 2/2009 | Weinstein | G06F 19/3418 600/300 |
| 2009/0276515 A1* | 11/2009 | Thomas | H04L 67/34 709/223 |
| 2011/0208540 A1* | 8/2011 | Lord | G06F 19/325 705/2 |
| 2012/0209625 A1 | 8/2012 | Armstrong et al. | |
| 2013/0275161 A1* | 10/2013 | Dutta | G06Q 10/06 705/3 |
| 2014/0006057 A1* | 1/2014 | Rock | G06F 19/325 705/3 |

FOREIGN PATENT DOCUMENTS

| | | |
|---|---|---|
| JP | 2006510436 A | 3/2006 |
| WO | 2005059803 A2 | 6/2005 |
| WO | 2012085719 A1 | 6/2012 |

* cited by examiner

METHOD AND SYSTEM FOR DETERMINING PATIENT STATUS

CROSS-REFERENCE TO PRIOR APPLICATIONS

This application is the U.S. National Phase application under 35 U.S.C. § 371 of International Application No. PCT/IB2013/058933, filed on Sep. 27, 2013, which claims the benefit of U.S. Provisional Application No. 61/707,168, filed on Sep. 28, 2012. These applications are hereby incorporated by reference herein.

Medical professionals typically guide their treatment of patients using clinical guidelines ("GLs"), which may be implemented as computer implemented guidelines ("CIGs") via clinical decision support ("CDS") systems. Typically, CIGs may be developed based on guidelines that are based on best available medical knowledge. CIGs may then be implemented for a specific system or environment, such as based on the capabilities of a specific care institution and the specific device that will be used to apply the CIGs. Thus, a change to an underlying guideline may result in changes to multiple system-specific CIGs; conversely, changes in localized system capabilities may require redesign of an existing set of CIGs without any change to the underlying GL. As a result, creation and updating of CIGs for different systems may be costly, and version management may be highly complex.

A system having a repository including a plurality of computer-implemented guidelines, an engine to execute one of the plurality of computer-implemented guidelines and a feature manager to receive an indication of a current state of the executing one of the computer-implemented guidelines, retrieve localization data that is specific to a hardware device, and instantiate a feature of the executing one of the computer-implemented guidelines on the hardware device based on the current state and the localization data.

A method for storing a computer-implemented guideline, wherein the computer-implemented guideline includes a plurality of device independent nodes, determining a current state of the computer-implemented guideline, wherein the current state relates to one of the device independent nodes, retrieving device features relating to a device on which the one of the device independent nodes of the computer-implemented guideline is to be performed, modifying the one of the device independent nodes based on the device features to generate a device specific node and instantiating the device specific node on the device.

A tangible computer readable medium that stores a set of instructions that is executable by a processor. The execution of the set of instructions causing the processor to perform a method for storing a computer-implemented guideline, wherein the computer-implemented guideline includes a plurality of device independent nodes, determining a current state of the computer-implemented guideline, wherein the current state relates to one of the device independent nodes, retrieving device features relating to a device on which the one of the device independent nodes of the computer-implemented guideline is to be performed, modifying the one of the device independent nodes based on the device features to generate a device specific node and instantiating the device specific node on the device.

Figure 1:
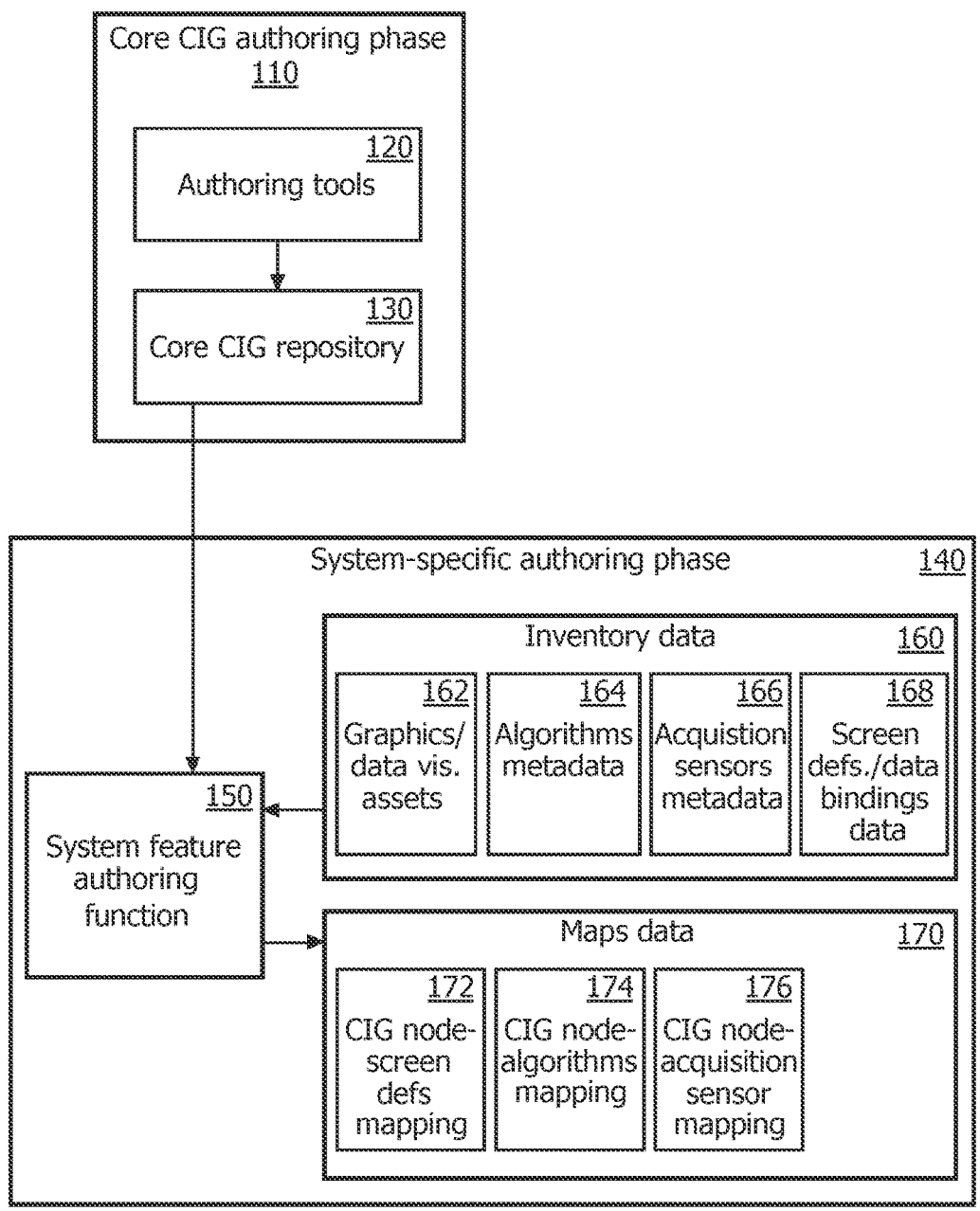
FIG. 1 illustrates an exemplary workflow for the creation of core CIGs and data required to implement core CIGs at specific system locations.

The exemplary embodiments may be further understood with reference to the following description of exemplary embodiments and the related appended drawings, wherein like elements are provided with the same reference numerals. Specifically, the exemplary embodiments relate to methods and systems for creating and propagating computer-implemented guidelines and related system components in an enterprise health care clinical decision support system.

Medical professionals typically guide their treatment of patients using clinical guidelines ("GLs"), which are recommendations, based on the best available evidence, of the appropriate treatment and care for people with specific diseases and conditions. GLs consist of decisions and decision criteria for diagnosis, management, and treatment of patients with the relevant diseases and conditions. Modern GLs represent evidence-based practices, i.e., they are based on clinical evidence acquired through scientific methods and studies such as randomized clinical trials.

Studies have shown that adhering to the recommendations of GLs reduces health care costs and improves outcomes. As a result, performance measures and reimbursements are increasingly related to guideline adherence. As a result of this relationship, it is desirable for health care solutions, and especially clinical decision support ("CDS") systems, to support the use of guidelines. For such support to be successful, it should fit seamlessly into existing clinical workflow. This may be accomplished by representing GLs, and localized care protocols derived therefrom, in a formalized way that can be interpreted by computers.

The resulting computer interpretable guidelines ("CIGs"), also known as executable clinical guidelines, are computer interpretable representations of the clinical knowledge contained in GLs. CIGs are executed by software known as a CIG engine. As part of, or invoked by, a CDS system, a CIG engine applies the logic of a CIG to patient data and user inputs to generate recommendations for care providers. An individual CIG typically models a care process for one type of disease or condition, and for a particular type of care environment tailored to a specific care institution. CIGs are also often developed for a specific type of system, making assumptions on system capabilities such as the presence of data acquisition, the available screen resolution, audio signaling, and data processing algorithms.

Increasing numbers of CDS systems are applying CIGs. Since CIGs are often developed for a particular type of system and clinical domain, they have to be redesigned in order to be used for other systems. As a result, a change to a GL may result in changes to multiple system-specific CIGs. Similarly, changes in system capabilities may require redesign of an existing set of CIGs without any change to the underlying GL. Therefore, creation and updating of CIGs for different systems may be costly, and version management may be highly complex. The exemplary embodiments provide a solution that enables CIGs to be created independently from any specific application or system type, while CIG-dependent behavior, user interaction, data processing and visualization can be tailored to the application, system type, and deployment, without impacting the current base of CIGs.

The exemplary embodiments use core CIG components that capture essential GL knowledge. "Core" CIG components are created and maintained by a set of authoring tools. CIG-related system-specific features are created, configured, and maintained by a set of authoring tools for each specific system type. CIG-related system-specific features are integrated into specific systems by infrastructure components. Therefore, a core CIG does not contain any system-specific information, but, rather, only contains parameterized nodes (representing care steps), rules, and recommendations from clinical knowledge. As noted above, the core CIG is created through a process of knowledge acquisition and authoring, and using a set of authoring tools. System-specific features are separately defined through system-specific authoring steps. Most frequently, system-specific features include the graphical user interface (e.g., the screen layout, screen elements, and data visualizations), the data processing/analysis algorithms (which typically depend on the type of care, and hence are CIG dependent), and the acquisition of patient data (e.g., sensor data, biometric measurements, and access to electronic medical records).

FIG. 1 illustrates a schematic representation of an exemplary workflow 100 for creation of core CIGs and adaptation of the core CIGs to system-specific versions. The workflow 100 is divided into two phases: the core CIG authoring phase 110 and the system-specific authoring phase 140. As described above, during the core CIG authoring phase 110, core (i.e. system-independent) CIGs are created using a set of authoring tools 120. The authoring tools 120 may present a CIG author with a model allowing the author to formalize the interpretation of a GL into a CIG. The authoring tools 120 may allow the author to define key components including rules (e.g., in the form of if/then statements) and states (e.g., determining a status of care). The authoring tools 120 thus allow the author to manually specify the rules of a GL in a formal way such that the result is a CIG that formally represents a GL. The authoring tools 120 may include screens where the author specifies roles and a workflow/careflow for a particular disease or condition. Each node of a core CIG may be represented using a unique identifier.

Once a core CIG is defined using authoring tools 120, it may be stored in a core CIG repository 130, which may be maintained by, for example, a hospital, a network of hospitals, a provider of CDS services, or any other appropriate entity. The core CIG repository 130 stores the newly-created core CIG along with other previously-created core CIGs. In another embodiment, the authoring tools 120 may be used to modify an existing core CIG (e.g., due to changes in medical or scientific knowledge), and the CIG repository 130 may replace the existing version with the updated version.

The second phase of the workflow 100 is the system-specific authoring phase 140, which may take place, for example, locally at a hospital site. The system-specific authoring phase 140 is coordinated by a system feature authoring function 150, which may use various types of system-specific data to adapt a core CIG into a system-specific CIG. The system specific data includes inventory data 160 and maps data 170. The inventory data 160 includes graphics and data visualization assets 162 relating to the graphical and visualization capabilities of the specific system, algorithms metadata 164 relating to the algorithmic performance capabilities of the specific system, acquisition sensors metadata 166 relating to the capabilities of the local system to capture data, and screen definitions/data bindings data 168.

The system feature authoring function 150 receives a CIG from the core CIG repository 130, along with the various inventory data 160, and creates maps data 170 for mapping the performance of a CIG to the specific system. The maps data 170 includes CIG node to screen definitions mapping 172 providing for the mapping of display/output elements of a CIG to the display of the specific system, CIG node to algorithms mapping 174 for the mapping of algorithmic determinations of a CIG to the algorithmic performance by the specific system, and CIG node to acquisition sensor mapping 176 for the mapping of data inputs by a CIG to the data acquisition sensors of the specific system. Overall, the maps data 170 describe the screens, algorithms and data acquisitions which must be activated or deactivated based on the status of the nodes of the core CIG. Using the inventory data 160 and the maps data 170, system-specific CIG implementation may be accomplished using a CIG engine, as described above. The CIG engine may provide for the consistent performance of a core CIG for a single patient across multiple devices, each of which uses a system-specific version of the core CIG.

Figure 2:
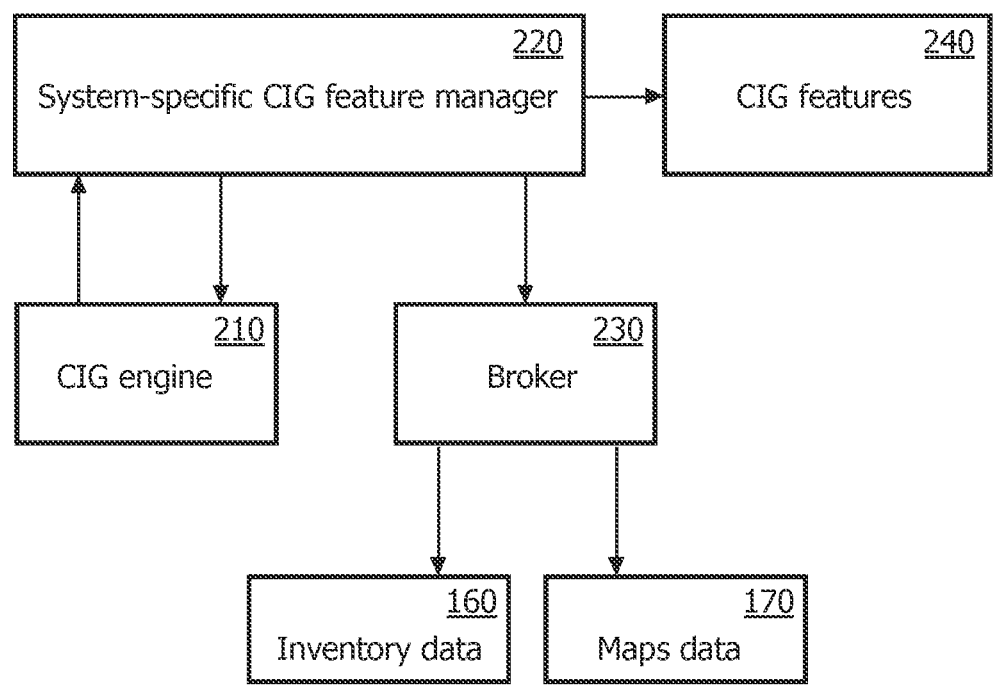
FIG. 2 illustrates an exemplary system architecture for the application of a core CIG at an exemplary system location.

FIG. 2 illustrates the performance of an exemplary architecture 200 including a CIG engine 210, which may be implemented by a CDS system as described above. The CIG engine 210 may operate in conjunction with a plurality of system-specific CIG feature managers 220, which may each be implemented by a specific device implementing a system-specific version of the same core CIG for the treatment of a patient. Each of the system-specific CIG feature managers 220 starts and stops related features, which may be, for example, displays, data processing algorithms, or data acquisition tasks. The system-specific CIG feature managers 220 may use a broker 230 to retrieve appropriate features. The broker 230 retrieves the appropriate feature definitions (e.g., screen definitions, data processing algorithm input/output definitions, location of executables, acquisition sensor access-point definitions) from the inventory data 160, which contains actual feature definitions, and maps data 170, which contains data for mapping the feature to the specific system, as described above.

Thus, as described above, any number of system-specific CIG feature managers 220 may be running on any corresponding devices that may work together to implement a CIG. The system-specific CIG feature managers 220 may constantly listen for CIG state change events from the CIG engine 210. When a state change event occurs, each system-specific CIG feature manager 220 retrieves the set of all CIG nodes from the CIG engine 210, and, thus, knows the state of the performance of the CIG. Each system-specific CIG feature manager 220 retrieves appropriate features using the broker 230, and may then instantiate CIG features 240 (e.g., may display a screen to a user, run an algorithm, or activate a sensor). The general framework described above and illustrated in FIG. 2 may be used at various points in a CIG-based health care enterprise system to enable the seamless application of a CIG to the treatment of a patient across various devices that are used to perform differing tasks.

To provide one specific non-limiting example, a patient may arrive at an emergency room of a hospital with the symptoms of a heart attack. These symptoms may trigger the CIG engine 210 to run a specific CIG for the treatment of a patient suffering from a heart attack. The broker 230 will then retrieve the appropriate features from inventory data 160 and maps data 170 (e.g., stored in a server dedicated to implementing a CDS system) to enable CIG feature manager 220 to display or otherwise execute the CIG on the systems in the emergency room. As the various steps of procedures of the CIG are performed or data is received, the CIG engine 210 will indicate a change of state for the CIG and the CIG feature manager 230 will retrieve the features based on the change of state. At some point the patient may be transferred to a cardiac laboratory in the hospital that has different systems from the emergency room. However, the same CIG will continue to be executed for the patient. When the patient arrives at the cardiac lab, the CIG feature manager 220 of a system present in the cardiac lab will use its own broker 230 to retrieve the appropriate features from inventory data 160 and maps data 170 for the CIG feature manager 220 present on systems in the cardiac lab to display or otherwise execute the same CIG on the systems of the cardiac lab; the same CIG engine 210, which may also be stored in a server dedicated to implementing a CDS system, continues to govern the overall performance of the CIG.

Figure 3:
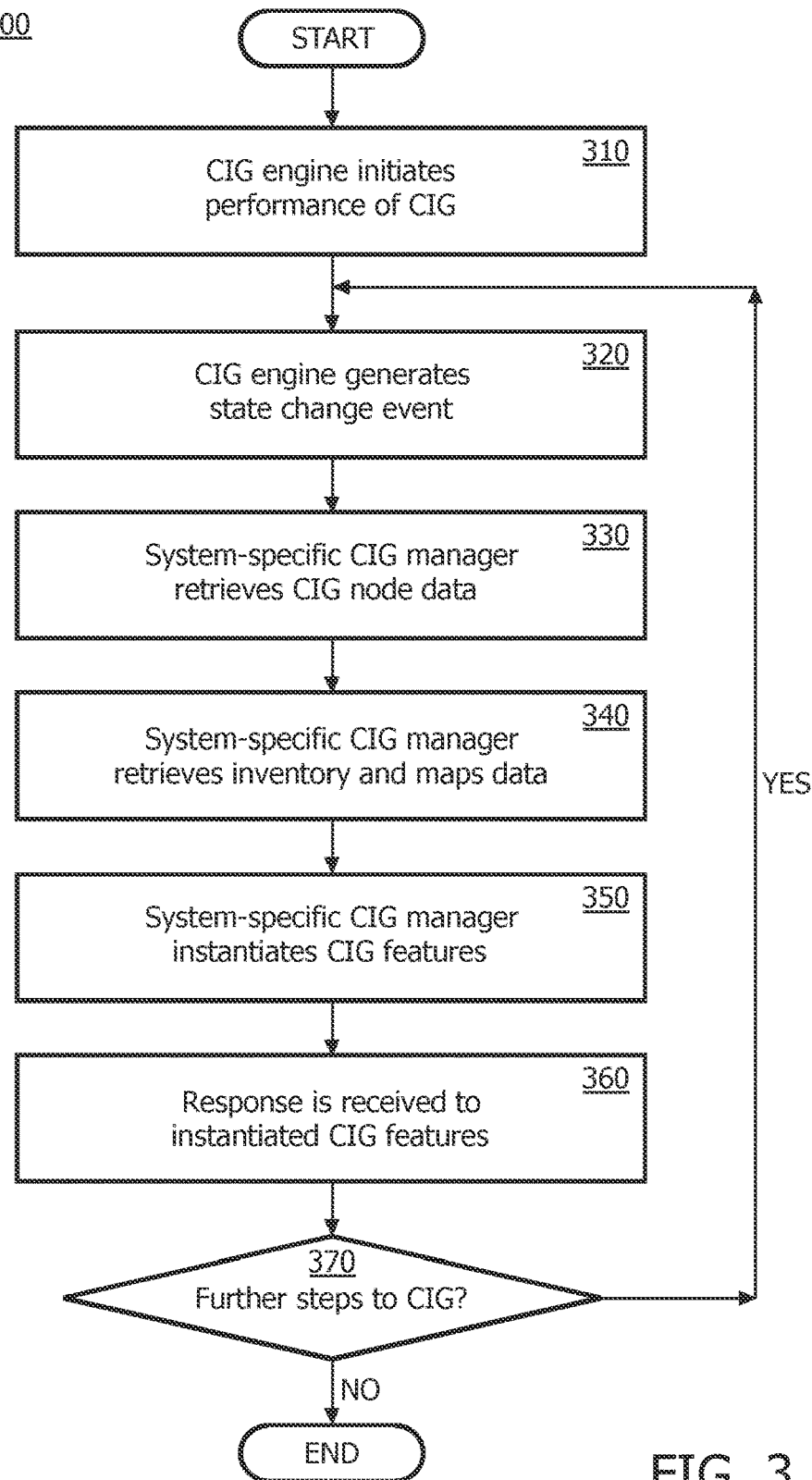
FIG. 3 illustrates an exemplary method for the application of a core CIG at an exemplary system location using the exemplary system architecture of FIG. 2.

FIG. 3 illustrates an exemplary method 300 by which an exemplary system architecture, such as the architecture 200 of FIG. 2, may operate to apply a core CIG at a specific system location. The method 300 will be described with specific reference to the elements of the architecture 200, but those of skill in the art will understand that similar methods may be implemented on differing types of system architecture without departing from the broader principles outlined herein; for example, a similar method may be executed by architecture 400, which will be described hereinafter. In step 310, CIG engine 210 begins the execution of a CIG; this may be prompted, for example, by the commencement of treatment of a patient having a condition relevant to the CIG being executed. In step 320, CIG engine 210 generates a state change event relating to the current node (i.e., stage of treatment) of the CIG.

In step 330, responding to the state change event, the system-specific CIG feature manager 220 retrieves CIG node data from CIG engine 210 and, thus, becomes aware of the current state of the performance of the CIG. Those of skill in the art will understand that, while the method 200 will be described with reference to a single system-specific CIG feature manager 220, a separate system-specific CIG feature manager 220 may operate on each individual device involved in performing the CIG, such as a patient vital signs sensor, a patient vital signs monitor, a nurse handheld device, etc.

Next, in step 340, the system-specific CIG feature manager 220 retrieves, via broker 230, appropriate inventory data 160 and maps data 170 for the instantiation of CIG features on the device governed by the system-specific CIG feature manager 220. Based on the retrieved data and the current state of the CIG, in step 350 the system-specific CIG feature manager 220 will then instantiate the appropriate CIG feature or features. For example, if the current node of the CIG calls for the measuring of the patient's blood pressure, a system-specific CIG feature manager 220 executing on a vital signs monitor will retrieve features for performing such a measurement and will record the patient's blood pressure; in contrast, a system-specific CIG feature manager 220 executing on a bedside display providing instructions to medical professionals will not retrieve any relevant features, and will not instantiate any CIG features.

In step 360, a corresponding response to the instantiated CIG features is received. Those of skill in the art will understand that the appropriate response will vary based on the nature of the instantiated CIG features. For example, for the measuring of a patient vital sign, the response will be the measured vital sign; for a request for information from a medical professional, the response will be the receipt of manual input; for a display or audio alert providing information to a medical professional, the response may be the receipt of an acknowledgement of the display or audio alert, or may be no required response at all. After the appropriate CIG features have been instantiated and the response has been received, the state of the CIG will be updated accordingly. Once this has occurred, in step 370 the CIG engine 210 determines whether the CIG has further steps. If the CIG continues, the method returns to step 320, where the CIG engine generates a next appropriate state change event. In contrast, if there are no further steps to the CIG, then the method 300 terminates after step 370. In some exemplary embodiments, a CIG output (e.g., a therapy recommendation, a recommended medication and dosage, an indication that the patient is healthy, etc.) may be generated and provided to health care professionals prior to the termination of the method 300.

Figure 4:
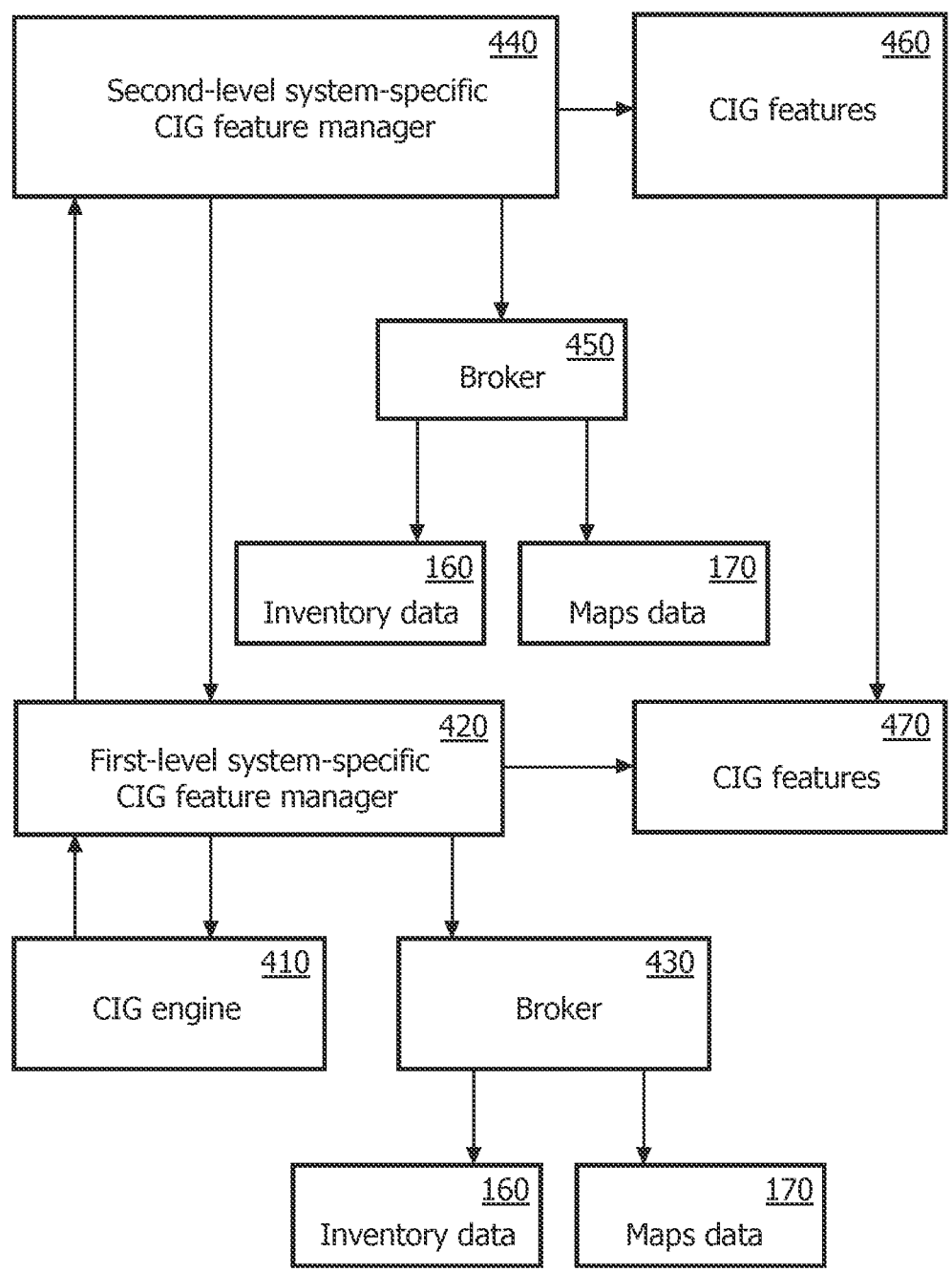
FIG. 4 illustrates a further exemplary system architecture for the application of a core CIG at a further exemplary system location.

FIG. 4 illustrates an exemplary architecture 400, which is similar to the architecture 200 of FIG. 2, but is stacked in a manner such that one feature manager depends on another, as will be described in further detail below. As described above, CIG engine 410 generates a state that is detected by the first-level system-specific CIG feature manager 420, and, in response, first-level system-specific CIG feature manager 420 retrieves the set of all CIG nodes from the CIG engine 410. Also as above, first-level system-specific CIG feature manager 420 consults broker 430 to obtain a proper screen definition for the appropriate CIG nodes.

Next, first-level system-specific CIG feature manager 420 informs second-level system-specific CIG feature manager 440 of the change in state, which will be referred to herein as a "screen change". In response, the second-level system-specific CIG feature manager 440 retrieves the list of screen elements referred to by the current screen change from first-level system-specific CIG feature manager 420. Once this data has been received, the second-level system-specific CIG feature manager 440 uses broker 450 to retrieve the class definition for the appropriate CIG nodes. Based on the data retrieved using the broker 450, the second-level system-specific CIG feature manager 440 instantiates appropriate second-level features 460. These may be, for example, sub-features of the first-level features 470 to be presented by the first-level system-specific CIG feature manager 420. The second-level system-specific CIG feature manager 440 then passes references to its instantiated features to the first-level system-specific CIG feature manager 420, and the first-level system-specific CIG feature manager 440 builds its user interface and other related elements using both its own features and those of the second-level system-specific CIG feature manager 440.

Figure 5:
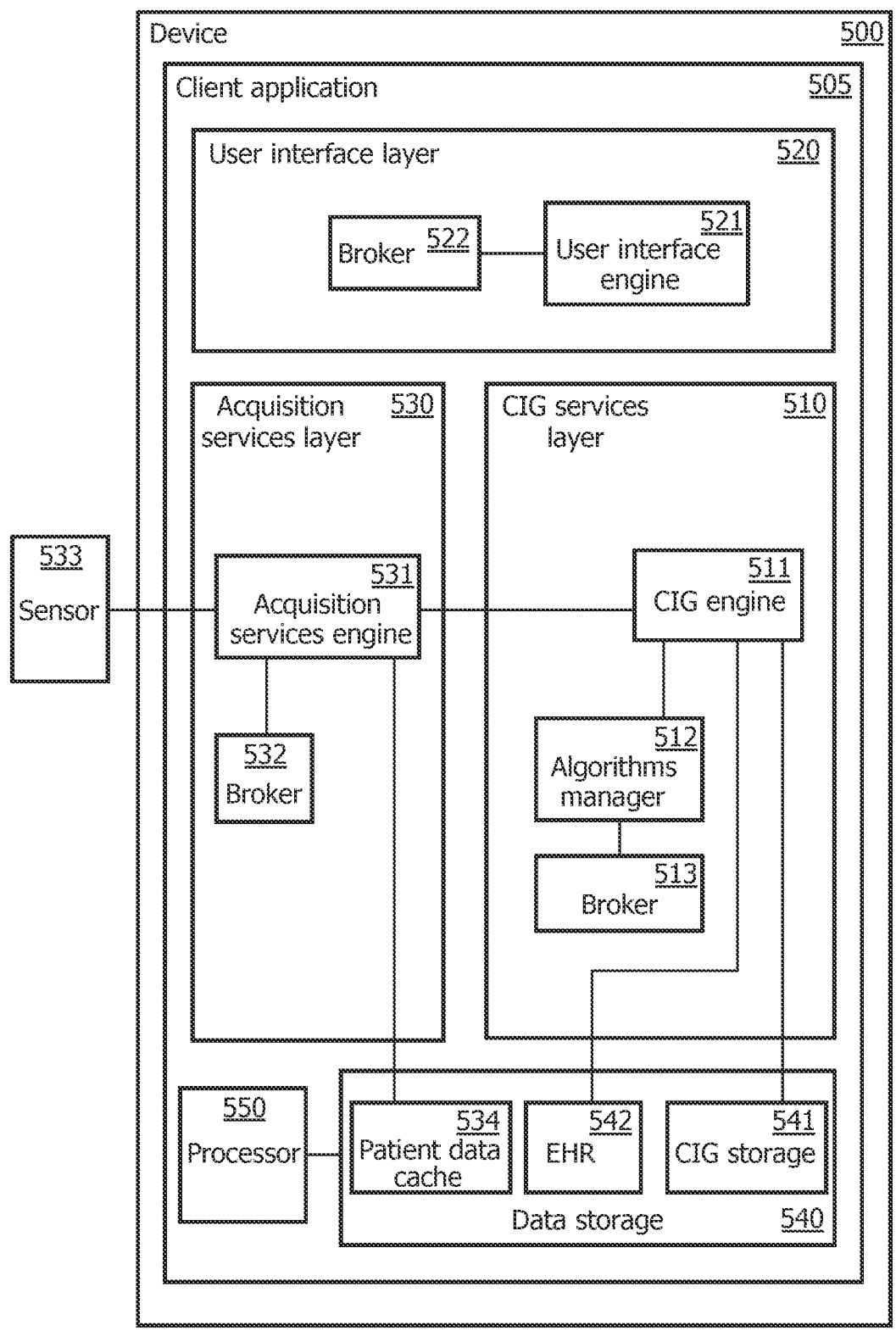
FIG. 5 illustrates an exemplary device implementing a CIG.

As described above, a feature manager may be implemented in various places within CIG-based health care systems. FIG. 5 illustrates the implementation of a feature manager in a standalone user device 500 running client application 505 with no external connectivity; those of skill in the art will understand that this is only one exemplary embodiment, and that an enterprise solution within a networked environment is also possible. The client application 505 includes a CIG services layer 510, a user interface layer 520, an acquisition services layer 530, a data storage 540, and a processor 550 executing software to operate the layers noted above. The CIG services layer 510 includes a CIG engine 511 as described above. The CIG engine 511 accesses a CIG repository 541 stored within data storage 540 to coordinate the execution of a CIG. The CIG services layer 510 also includes an algorithms manager 512 which coordinates the execution of any data processing algorithms that are part of the CIG being executed; the algorithms manager 512 uses a broker 513, as described above, to access data relating to the implementation of the CIG on the specific device 500. The CIG engine 511 may also consult, as needed, a patient electronic health record ("EHR") 542, stored within data storage 540, where necessary to determine the course of treatment for the patient.

The user interface layer 520 includes a user interface engine 521 in communication with the CIG engine 511; in other exemplary embodiments, the user interface layer 520 may include a CIG services interface layer for interfacing with the CIG services layer 510. The user interface engine 521 receives information relating to the performance of the CIG from the CIG engine 511, and instantiates user interface objects (e.g., controls, forms, data visualizations, etc.) where appropriate. To accomplish this, the user interface engine 521 uses a broker 522, as described above, to retrieve inventory data and maps data relating to the implementation of the CIG on the specific device 500.

The acquisition services layer 530 includes an acquisition services engine 531 in communication with the CIG engine 511. The acquisition services engine 531 receives information relating to the performance of the CIG from the CIG engine, and performs data acquisition in accordance with the capabilities of the device 500. The acquisition services engine 531 uses a broker 532 to retrieve inventory data and maps data relating to the implementation of the CIG on the specific device 500. Based on the instructions received from CIG engine 511 and using data retrieved by broker 532, the acquisition services engine communicates with sensors 533, which may be internal or external to the device 500, to acquire patient data, and stores the data in patient data cache 534, within data storage 540. Thus, the CIG engine 511 may coordinate the performance of a CIG by the CIG services layer 510, the user interface layer 520, and the acquisition services layer 530, with each layer having its own broker to obtain data relating to the localization of the core CIG in the user device 500.

The exemplary embodiments described above may provide for the implementation of CIGs in an environment in which a core CIG may be authored in a manner that is independent from its implementation on various systems or in various care environments. Such authoring may be beneficial because the validation of a core CIG may be a costly and/or time-consuming process, and complete re-authoring for each individual system is therefore not feasible. Core CIGs are then implemented into various environments, using a system feature authoring function as described above, without impacting the status of the core CIG itself, and in a manner that is simpler than modifying the core CIG. As a result, CDS systems may use the best and most current knowledge from a core CIG, which are customized for the specific parameters of the CDS system, its environment, and the devices therein. The exemplary embodiments also provide for a mechanism whereby a device or multiple devices operating within a given CDS system may use a CIG in accordance with the methods described above.

Those of skill in the art will understand that the above-described exemplary embodiments may be implemented in any number of matters, including as a software module, as a combination of hardware and software, etc. For example, the exemplary system feature authoring function 150, the exemplary CIG engine 210, and the system-specific CIG feature manager 220, among other elements of the exemplary embodiments, may be embodied in a program stored in a non-transitory storage medium and containing lines of code that, when compiled, may be executed by a processor.

It is noted that the claims may include reference signs/numerals in accordance with PCT Rule 6.2(b). However, the present claims should not be considered to be limited to the exemplary embodiments corresponding to the reference signs/numerals.

It will be apparent to those skilled in the art that various modifications may be made to the exemplary embodiments, without departing from the spirit or the scope of the invention. Thus, it is intended that the present invention cover modifications and variations of this invention provided they come within the scope of the appended claims and their equivalents.

What is claimed is:

1. A clinical decision support (CDS) system, comprising:
   a repository including a plurality of core computer-implemented clinical guidelines (CIGs), wherein each core CIG comprises a plurality of device-independent computer-implemented nodes corresponding to steps of a care process predetermined by a clinical guideline (GL);
   an engine configured to execute by a processor a selected one of the plurality of core CIGs across a plurality of hardware devices, wherein each hardware device utilizes one or more hardware-specific features corresponding to at least one node, the selected core CIG being mapped to the device; and
   a plurality of hardware-specific feature managers which are processor-executable, each feature manager corresponds to one of the plurality of hardware device and is configured to: receive an indication of a current state of execution of the selected core CIG, retrieve localization data specific to the corresponding hardware device, wherein the localization data includes capabilities of the corresponding hardware device, and instantiate a hardware-specific feature configured to map at least one node of the selected core CIG to the corresponding hardware device based on the current state and the localization data,
   wherein the plurality of hardware-specific feature managers comprises a first feature manager configured to retrieve first localization data of a first one of the plurality of hardware devices, and a second feature manager configured to retrieve second localization data of a second one of the plurality of hardware devices, the first localization data being different from the second localization data, and
   wherein a first feature instantiated by the first feature manager is different from a second feature by the second feature manager.

2. The system of claim 1,
   wherein the engine is configured to receive a response from the hardware devices, and change the current state to an updated state of execution of the selected core CIG, and
   wherein each feature manager is configured to: receive an indication of the updated state, retrieve further localization data specific to the corresponding hardware device, wherein the further localization data includes capabilities of the corresponding hardware device, and instantiate a further hardware-specific feature configured to map at least one node of the selected core CIG to the corresponding hardware device based on the updated state and the further localization data.

3. The system of claim 1, wherein the feature manager is configured to retrieve the localization data via a broker.

4. The system of claim 1, wherein the capabilities of the corresponding hardware device include one of graphics assets, data visualization assets, algorithmic performance capabilities, acquisition sensors, screen definitions and data binding data.

5. The system of claim 1, wherein the localization data includes mapping information which includes one of a computer-implemented clinical guideline node to screen definition mapping, a computer-implemented clinical guideline node to algorithm mapping and a computer-implemented clinical guideline node to acquisition sensor mapping.

6. The system of claim 1, wherein the first corresponding hardware device is controlled based on the first feature, and the second corresponding hardware device is controlled based on the second feature.

7. A method for computer-implemented clinical diagnosis and treatment of a patient across a plurality of devices, comprising:
    storing a core computer-implemented clinical guideline (CIG), wherein the core CIG includes a plurality of device-independent nodes corresponding to steps of a care process predetermined by a clinical guideline (GL);
    determining a current state of the core CIG by a processor, wherein the current state relates to one of the device-independent nodes;
    receiving, by each of a plurality of hardware-specific feature managers, the current state of the core CIG, wherein each feature manager corresponds to one of the plurality of devices;
    retrieving device features relating to the devices on which the device-independent nodes of the core CIG are to be performed, wherein the device features include capabilities of the devices, and wherein a first feature manager retrieves first device features corresponding to a first one of the devices, and a second feature manager retrieves second device features corresponding to a second one of the devices, the first device features being different from the second device features;
    modifying one of the device-independent nodes of the core CIG based on device features of the first device to generate a first device-specific node, and modifying another one of the device-independent nodes of the core CIG based on device features of the second device to generate a second device-specific node; and
    instantiating by a processor the first device-specific node on the first device and the second device-specific node on the second device, the first instantiation being different from the second instantiation.

8. The method of claim 7, further comprising:
    receiving a response from a selected one of the devices;
    determining an updated state of execution of the core CIG based on the response, wherein the updated state relates to a further one of the device-independent nodes;
    retrieving further device features relating to the device, wherein the further device features include capabilities of the selected device;
    modifying one of the device-independent nodes based on the further device features to generate a further device-specific node; and
    instantiating the further device specific node on the selected device.

9. The method of claim 7, further comprising:
    receiving a response from a selected one of the devices;
    determining an updated state of execution of the core CIG based on the response, wherein the updated state relates to a further one of the device independent nodes;
    retrieving further device features relating to a further one of the devices on which a further one of the device-independent nodes is to be performed, wherein the further device features include capabilities of the further device;
    modifying the further one of the device independent nodes based on the further device features to generate a further device specific node; and
    instantiating the further device specific node on the further device.

10. The method of claim 7, further comprising:
    receiving a response from a selected one of the devices;
    determining an updated state of execution of the core CIG based on the response, wherein the updated state relates to a completion of the core CIG; and
    generating an indication of the completion of the core CIG.

11. The method of claim 7, wherein the capabilities of the device include one of graphics assets, data visualization assets, algorithmic performance capabilities, acquisition sensors, screen definitions and data binding data.

12. The method of claim 7, wherein the features include mapping information which includes one of a computer-implemented clinical guideline node to screen definition mapping, a computer-implemented clinical guideline node to algorithm mapping and a computer-implemented clinical guideline node to acquisition sensor mapping.

13. The method of claim 7, further comprising:
    controlling the first device based on the first device specific node, and controlling the second device based on the second device specific node, wherein the first and second devices are configured to obtain diagnostic data or administer a treatment to the patient.

14. A tangible computer readable memory to store a set of instructions executable by a processor to perform a method for computer-implemented clinical diagnosis and treatment of a patient across a plurality of devices, comprising:
    storing a core computer-implemented clinical guideline (CIG), wherein the core CIG includes a plurality of device independent nodes corresponding to steps of a care process predetermined by a clinical guideline (GL);
    determining a current state of the core CIG by a processor, wherein the current state relates to one of the device independent nodes;
    receiving, by each of a plurality of hardware-specific feature managers, the current state of the core CIG, wherein each feature manager corresponds to one of the plurality of devices;
    retrieving device features relating to the devices on which the device-independent nodes of the core CIG are to be performed, wherein the device features include capabilities of the devices, and wherein a first feature manager retrieves first device features corresponding to a first one of the devices and a second feature manager retrieves second device features corresponding to a second one of the devices, the first device features being different from the second device features;
    modifying one of the device-independent nodes of the core CIG based on device features of the first device to generate a first device-specific node, and modifying another one of the device-independent nodes of the core CIG based on device features of the second device to generate a second device-specific node; and
    instantiating by a processor the first device specific node on the first device and the second device specific node on the second device, the first instantiation being different from the second instantiation.

15. The tangible computer readable memory of claim 14, wherein the method further comprises:
receiving a response from a selected one of the devices;
determining an updated state of execution of the core CIG based on the response, wherein the updated state relates to a further one of the device-independent nodes;
retrieving further device features relating to the device, wherein the further device features include capabilities of the selected device;
modifying one of the device independent nodes based on the further device features to generate a further device specific node; and
instantiating the further device specific node on the selected device.

16. The tangible computer readable memory of claim 14, wherein the method further comprises:
receiving a response from a selected one of the device;
determining an updated state of execution of the core CIG based on the response, wherein the updated state relates to a further one of the device independent nodes;
retrieving further device features relating to a further one of the devices on which the further one of the device-independent nodes is to be performed, wherein the further device features include capabilities of the further device;
modifying the further one of the device independent nodes based on the further device features to generate a further device specific node; and
instantiating the further device specific node on the further device.

* * * * *